United States Patent
Kast et al.

(10) Patent No.: US 6,505,077 B1
(45) Date of Patent: Jan. 7, 2003

(54) IMPLANTABLE MEDICAL DEVICE WITH EXTERNAL RECHARGING COIL ELECTRICAL CONNECTION

(75) Inventors: John E. Kast, Hugo, MN (US); Charles E. Peters, Blaine, MN (US); Jeffrey J. Clayton, Ramsey, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/596,211

(22) Filed: Jun. 19, 2000

(51) Int. Cl.$^7$ ................................. A61N 1/36
(52) U.S. Cl. ....................................... 607/61
(58) Field of Search .................... 607/61, 33, 55, 607/56, 57

(56) References Cited

U.S. PATENT DOCUMENTS

| | | | |
|---|---|---|---|
| 4,014,346 A | * | 3/1977 | Brownlee et al. |
| 4,041,955 A | | 8/1977 | Kelly et al. ............... 128/419 |
| 4,071,032 A | * | 1/1978 | Schulman |
| 4,134,408 A | | 1/1979 | Brownlee et al. ........... 128/419 |
| 5,314,457 A | | 5/1994 | Jeutter et al. ............... 607/116 |
| 5,411,537 A | | 5/1995 | Munshi et al. ............... 607/33 |
| 5,527,348 A | | 6/1996 | Winkler et al. ............... 607/30 |
| 5,562,714 A | | 10/1996 | Grevious ................... 607/32 |
| 5,733,313 A | | 3/1998 | Barreras, Sr. et al. ......... 607/33 |
| 5,861,019 A | | 1/1999 | Sun et al. .................. 607/60 |

FOREIGN PATENT DOCUMENTS

| | | |
|---|---|---|
| EP | 0499939 A1 | 2/1992 |
| EP | 0811395 A2 | 12/1997 |
| WO | WO 98/37926 | 9/1998 |
| WO | WO 99/06108 | 2/1999 |

OTHER PUBLICATIONS

Medtronic, Inc., "Implantable Neurostimulation Systems," 1998.
Sinha, Bunjan, "The Heart, Medicine and Health," Popular Science, p. 43, Feb. 2000.

* cited by examiner

Primary Examiner—Scott M. Getzow
(74) Attorney, Agent, or Firm—Tom Berry; Eric Waldkoetter; John Albrecht (57) ABSTRACT

A rechargeable implantable medical device with an improved external recharging coil electrical connection resistant to corrosion is disclosed. The electrical connection couples the external recharging coil to a recharge feedthrough. The rechargeable implantable medical device can be a medical device such as a neuro stimulator, drug delivery pump, pacemaker, defibrillator, diagnostic recorder, cochlear implant, and the like. The implantable medical device has a housing, electronics carried in the housing configured to perform a medical therapy, a rechargeable power source, and a recharging coil.

22 Claims, 9 Drawing Sheets

IMPLANTABLE MEDICAL DEVICE WITH EXTERNAL RECHARGING COIL ELECTRICAL CONNECTION

CROSS REFERENCE

The present application is related to the following copending applications entitled "Implantable Medical Device With External Recharge Coil" by inventors Kast et al. (attorney docket number P8970.00), "Implantable Medical Device With Recharging Coil Electro-Magnetic Shield" by inventors Kast et al. (attorney docket number P9399.00) which are not admitted as prior art with respect to the present invention by its mention in this cross reference section.

BACKGROUND OF THE INVENTION

This disclosure relates to an implantable medical device and more specifically to a rechargeable implantable medical device that produces a therapy for the human body.

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life. Examples of implantable medical devices include neuro stimulators, drug delivery pumps, pacemakers, defibrillators, diagnostic recorders, and cochlear implants. Some implantable medical devices provide therapies with significant power demands. To reduce the size of the power source and to extend the life of the power source, some of these implantable device can be recharged while implanted with a transcutaneous recharge signal.

Some implantable medical devices configured for recharging have a recharging coil that is external to the medical device housing for improved efficiency. The recharging coil can be attached to the exterior of the medical device housing or remotely located from the medical device housing. The recharging coil is electrically connected to electronics carried inside the medical device housing via recharge feedthroughs carried on the medical device housing. Typically the recharging coil is manufactured from a material with good electrical properties but with poor corrosion resistance when exposed to conditions in the human body. The electrical integrity of the electrical connection between the recharging coil and the recharge feedthroughs can be placed at risk by corrosion.

For the foregoing reasons there is a need for an implantable medical device improved electrical connection between an external recharging coil and recharging feedthroughs.

SUMMARY OF THE INVENTION

The implantable medical device improve external recharging coil electrical connection is resistant to corrosion and accomplished with at least one electrical connection having a recharge coil connection and a recharge feedthrough connection. The external recharging coil, that is carried external to the medical device housing, is electrically connected to the recharging coil connection, and the recharge feedthrough connection is electrically connected to the recharge feedthrough. The recharge feedthrough is electrically connected to electronics carried inside the medical device housing and also a rechargeable power source also carried inside the housing. The medical device housing also carries a therapy connection for delivering therapy to a patient.

BRIEF DESCRIPTION OF THE DRAWINGS

FIG. 5b shows an exploded view of the neuro stimulator embodiment shown in FIG. 5a;

FIG. 6b shows a recharging coil on the neuro stimulator embodiment shown in FIG. 6a;

FIG. 7b shows a recharging coil on the neuro stimulator embodiment shown in FIG. 7a;

DETAILED DESCRIPTION OF THE PREFERRED EMBODIMENTS

Figure 1:
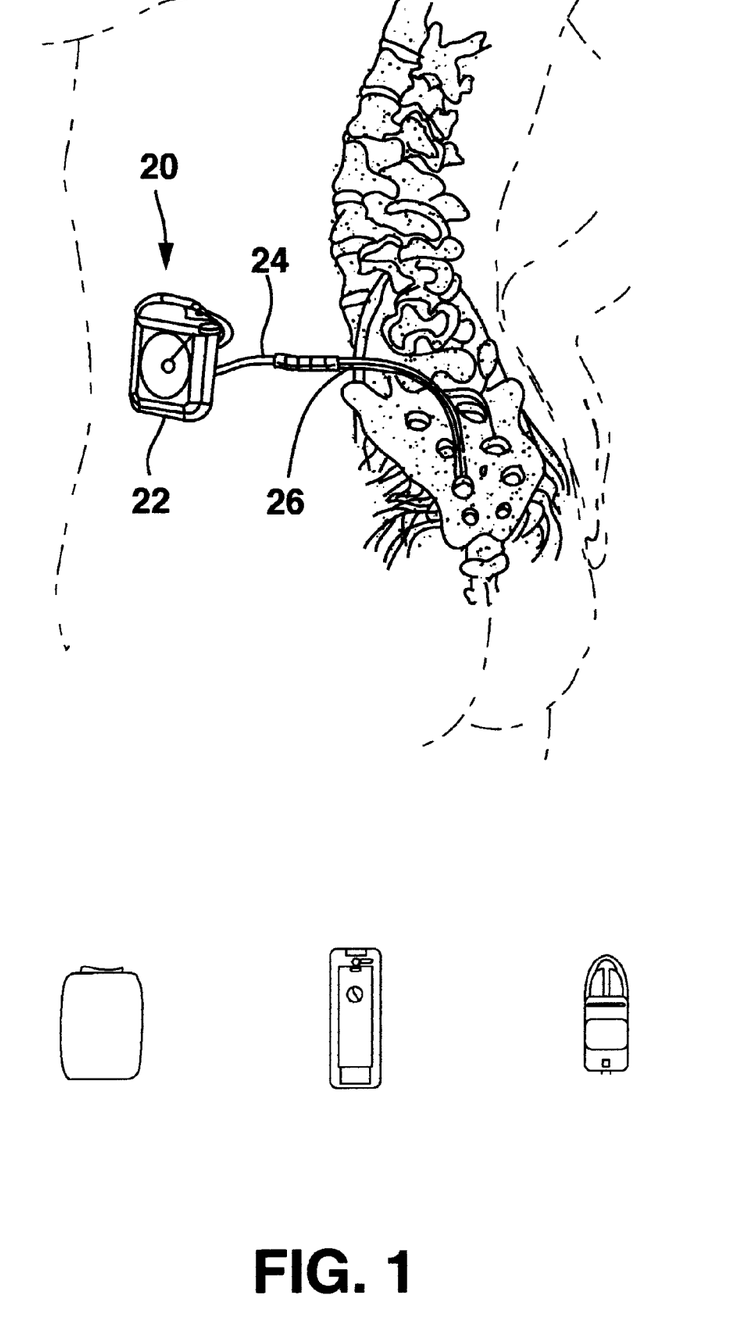
FIG. 1 shows an environment of a rechargeable implantable medical device embodiment.

FIG. 1 shows the general environment of one rechargeable implantable medical device 20 embodiment. An implantable neuro stimulator 22 is shown in FIG. 1, but other embodiments such as drug delivery pumps, pacemakers, defibrillators, diagnostic recorders, cochlear implants, and the like are equally applicable. Implantable medical devices 20 are often implanted subcutaneously approximated about one centimeter below the surface of the skin with an electrical lead or catheter extending to one or more therapy sites. The rechargeable implantable medical device 20 is recharged with a recharging device such as a patient charger or programmer that also has a charging capability.

Recharging an implanted medical device 20 generally begin with placing a recharging head containing a recharge coil near the proximal side of the medical device 20. Some rechargers have an antenna locator that indicates when the recharge head is aligned closely enough with the implanted medical device for adequate charge coupling. The recharge power transfer signal is typically a frequency in the range from 5.0 KHz to 10.0 KHz. The power transfer signal is converted into regulated DC power that is used to charge the power source. Once the recharge module fully changes the power source, the recharge module can be configured to serves as a power source for the implanted medical device while power is still received. Telemetry can also be conducted between the recharger and the implanted medical device 20 during recharging. Telemetry can be used aid in aligning the recharger with the implanted medical device 20, and telemetry can be used to manage the recharging process. Telemetry is typically conducted at a frequency in the range from 150 KHz to 200 KHz using a medical device telemetry protocol. For telemetry the recharger and implanted medical device 20 typically have a separate telemetry coil. The recharge coil can be multiplexed to also serve as a telemetry coil.

Figure 2:
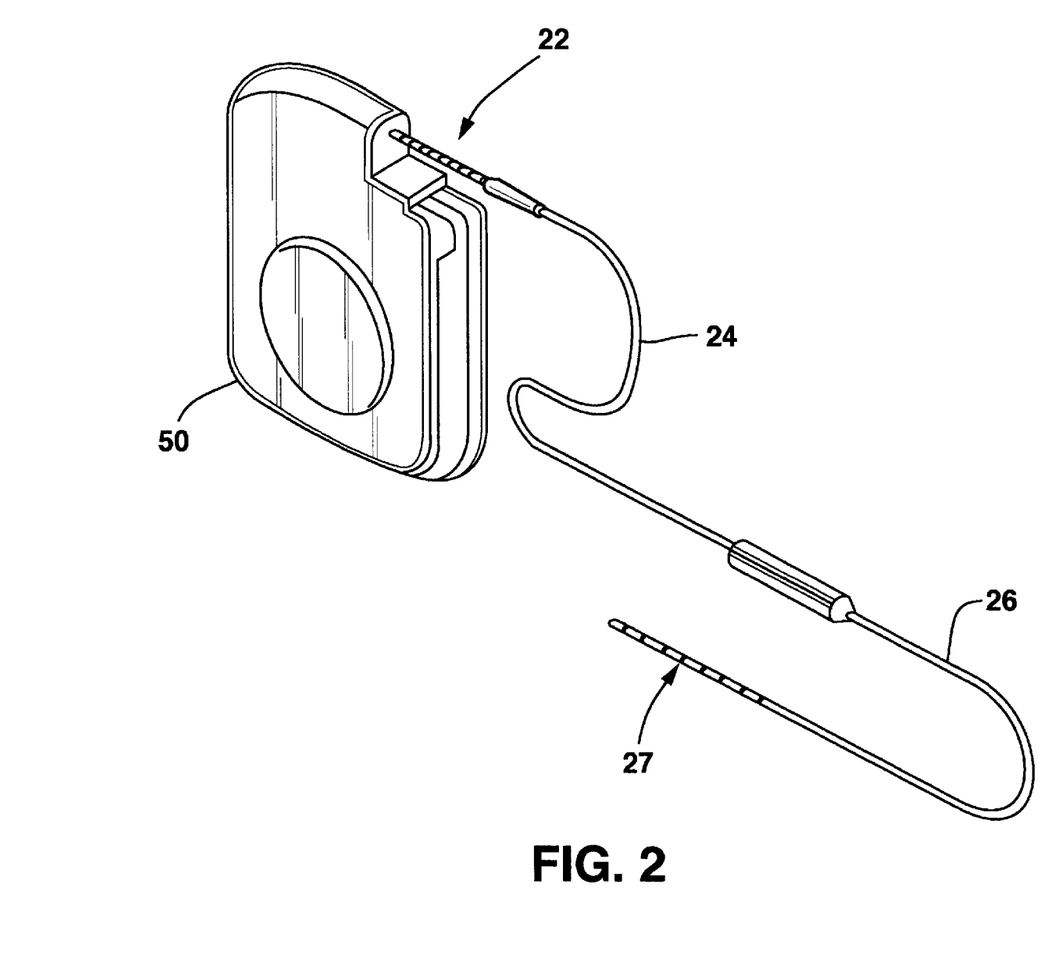
FIG. 2 shows a rechargeable implantable medical device neuro stimulator embodiment.
Figure 3:
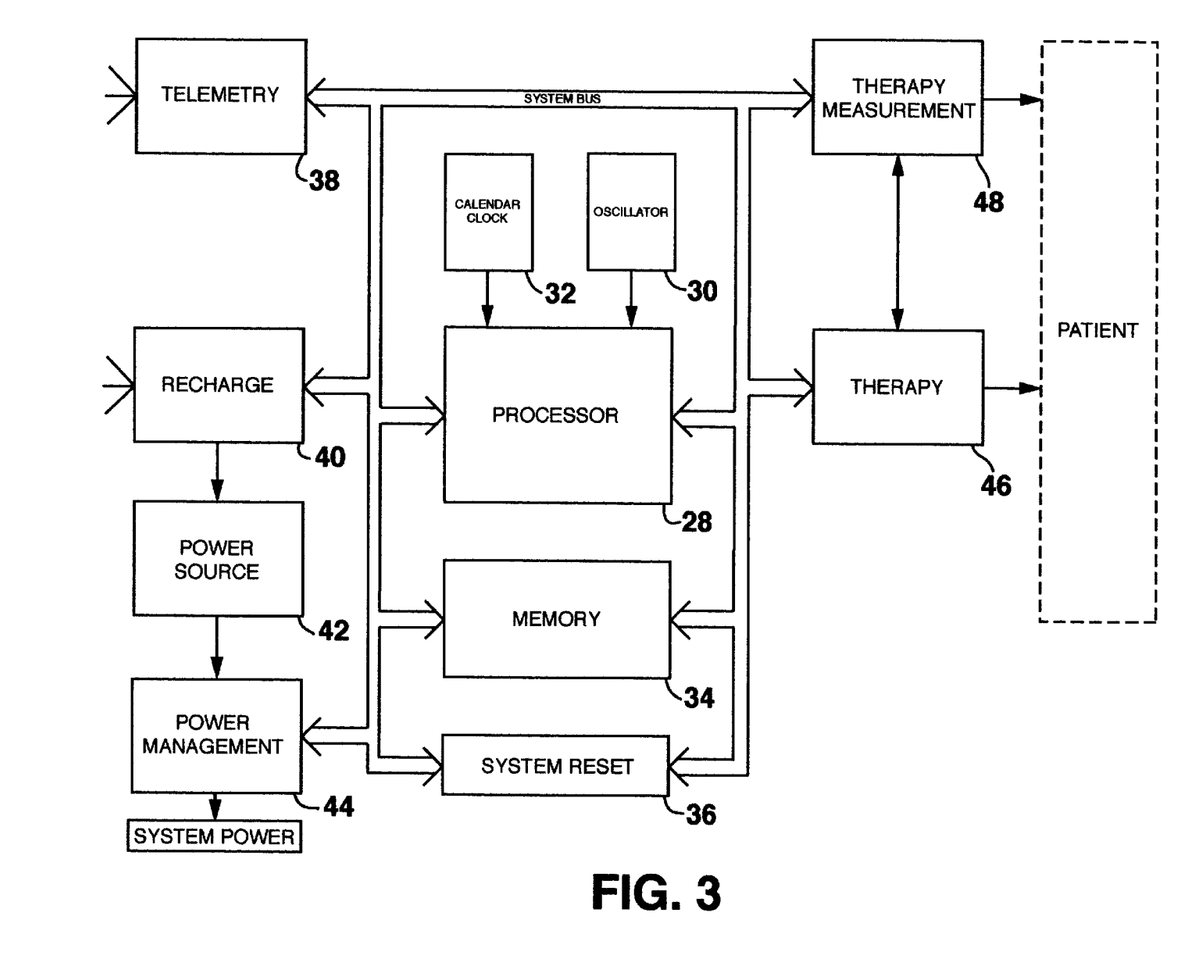
FIG. 3 shows a neuro stimulator electronics block diagram embodiment.

FIG. 2 shows a rechargeable implantable neuro stimulator 22 with a lead extension 24 and a lead 26 having electrical contacts 27. FIG. 3 shows a neuro stimulator electronics block diagram embodiment. The neuro stimulator 22 generates a programmable electrical stimulation signal. The neuro stimulator 22 electronics comprises a processor 28 with an oscillator 30, a calendar clock 32, memory 34, and system reset 36, a telemetry module 38, a recharge module 40, a power source 42, a power management module 44, a therapy module 46, and a therapy measurement module 48. All component of the neuro stimulator 22 are contained within or carried on a housing 50.

Figure 4:
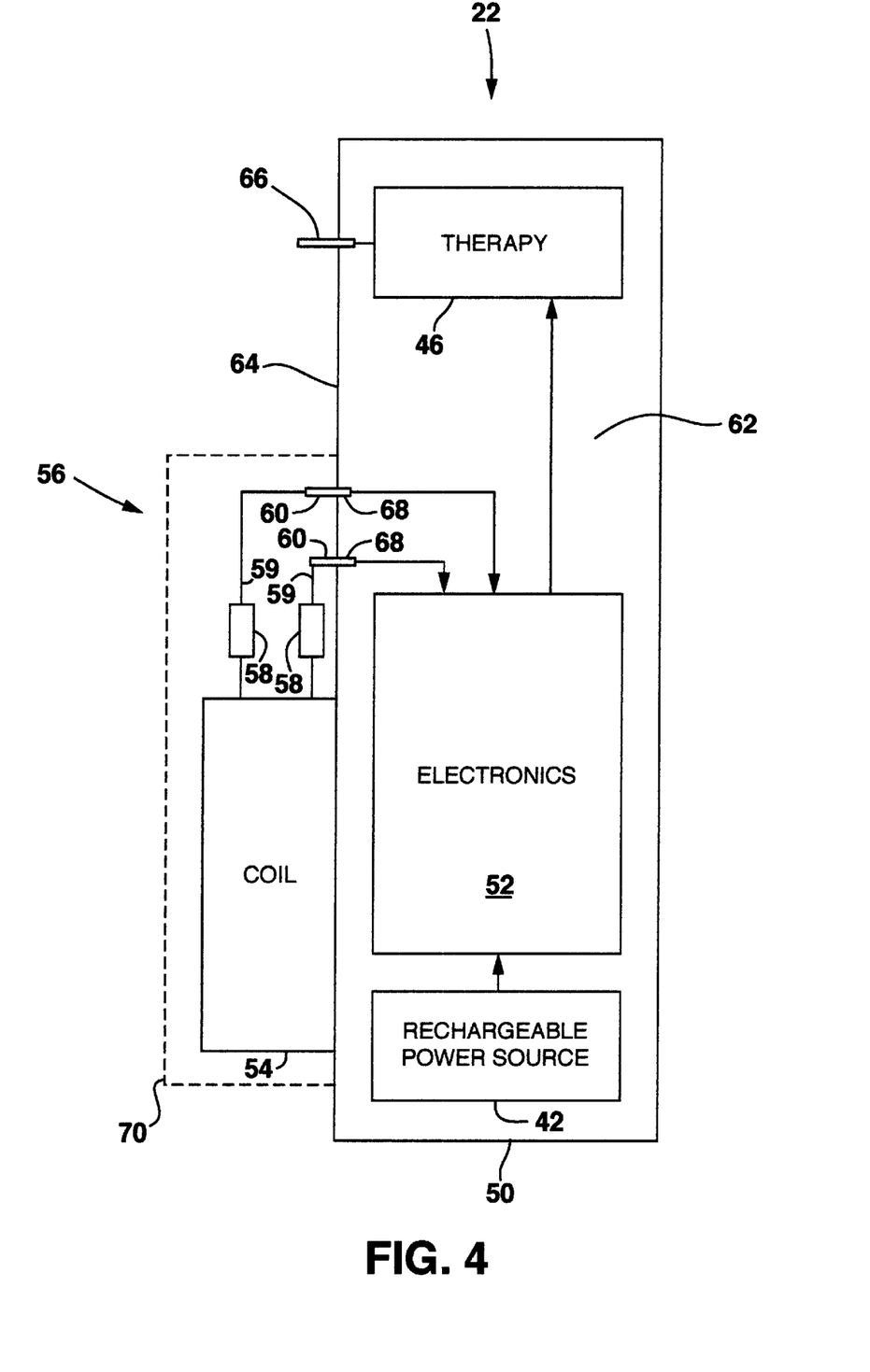
FIG. 4 shows a rechargeable implantable medical device block diagram embodiment.

FIG. 4 shows an implantable medical device 20 with recharging coil block diagram. The implantable medical device 20 with recharging coil electrical connection comprises a housing 50, electronics 52, a rechargeable power source 42, a recharge coil 54, and at least one electrical connection 56 having a recharge coil connection 58, a connection wire 59, and a recharge feedthrough connection 60. The housing 50 has an interior cavity 62, an exterior surface 64, a therapy connection 66, and a recharge feedthrough 68. The therapy connection 66 can be any type of therapy connection 66 such as a stimulation feedthrough, a drug infusion port, a physiological sensor, and the like. There can also be more than one therapy connection 66 and a combination of different types of therapy connections 66. The housing 50 is hermetically sealed and manufactured from a biocompatible material such as titanium, ceramic, epoxy, and the like. The housing 50 contains electronics 52.

The electronics 52 are carried in the housing interior cavity 62 and configured to perform a medical therapy. The electronics 52 are electrically connected to both a therapy module 46, and the recharge feedthrough 68. The rechargeable power source 42 is carried in the housing interior cavity 62 and coupled to the electronics 52. The rechargeable power source 42 can be a physical power source such as a capacitor or a chemical power source such as a battery. The battery can be a hermetically sealed rechargeable battery such as a lithium ion (L+) battery and the like. The electronics 52 are coupled to the recharging coil 54.

The recharging coil 54 is carried on the housing exterior surface 64 such as the proximal face of the medical device 20. The recharging coil 54 is manufactured from a material with electromagnetic properties such as copper wire, copper magnet wire, copper litz woven wire, gold alloy and the like. The recharging coil 54 can be manufactured from a wide variety of wire sizes such as wire diameters in the range from about 0.040 cm (26 AWG, American Wire Gauge) to 0.016 cm (34 AWG), or any other suitable diameter. The recharging coil 54 is coupled to the recharging feedthroughs 68 with an electrical connection 56.

The electrical connection 56 has a recharge coil connection 58, a connection wire 59, and a recharge feedthrough connection 60. The electrical connection 56 couples the recharge coil 54 to the recharge feedthrough 68 to couple the recharge coil 54 to the electronics 52. There is at least one electrical connection 56 and there can be additional electrical connections 56. The electrical connection 56 serves as a means for connecting the recharging coil 54 to the recharge feedthrough 68 to couple the recharging coil 54 to the electronics 52. The electrical connection 56 is composed of an inert conductive metal resistant to corrosion such as niobum, titanium, tantalum, and the like. Niobum (Nb) wire is available from Anomet Products, Inc., Shrewsbury, Mass. The electrical connection 56 includes a connection wire 59 selected to form an electrical connection between the recharge coil connection 58 and the recharge feedthrough connection 60 such as a wire diameter such as in the range from about 0.025 cm (24 AWG) to 0.051 cm (30 AWG) or any other suitable diameter composed of an inert conductive metal resistant to corrosion such as niobum, titanium, tantalum, and the like.

The recharge coil connection 58 is connected to the recharging coil 54 with a mechanical connection, a chemical connection, or a combination of both types of connection. The mechanical connection can be any mechanical connection that provides a physically connection and an electrical connection such as a crimp joint, a twist joint, or the like. The crimp joint can be manufactured from a material such as copper, niobium, titanium, and the like. The chemical connection can be chemical connection that provides a physical connection and an electrical connection such as a weld, braze joint, solider joint, or the like. A hermetic seal 70 is placed over the electrical connection 56.

The hermetic seal 70 for the electrical connection 56 protects the electrical connection 56 from being exposed to biological tissue or fluids. The hermetic seal 70 is a biocompatible material and can take may forms including potting material, epoxy, polysulforne, polyurethane, silicone rubber, polymer encapsulation, coil cover with polymer seal, and the like.

Figure 5A:
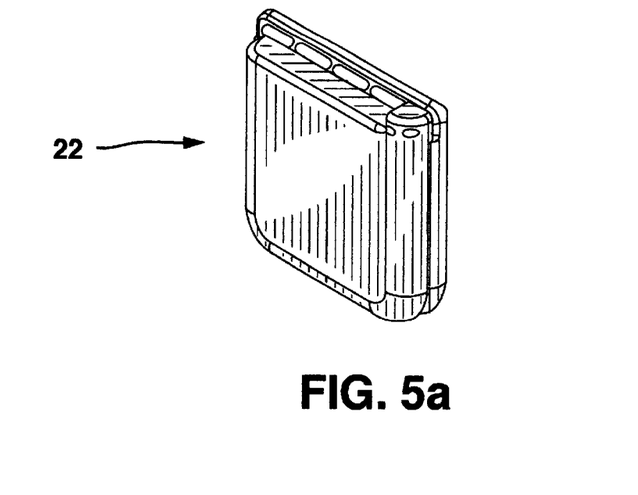
FIG. 5a shows a neuro stimulator embodiment.
Figure 5B:
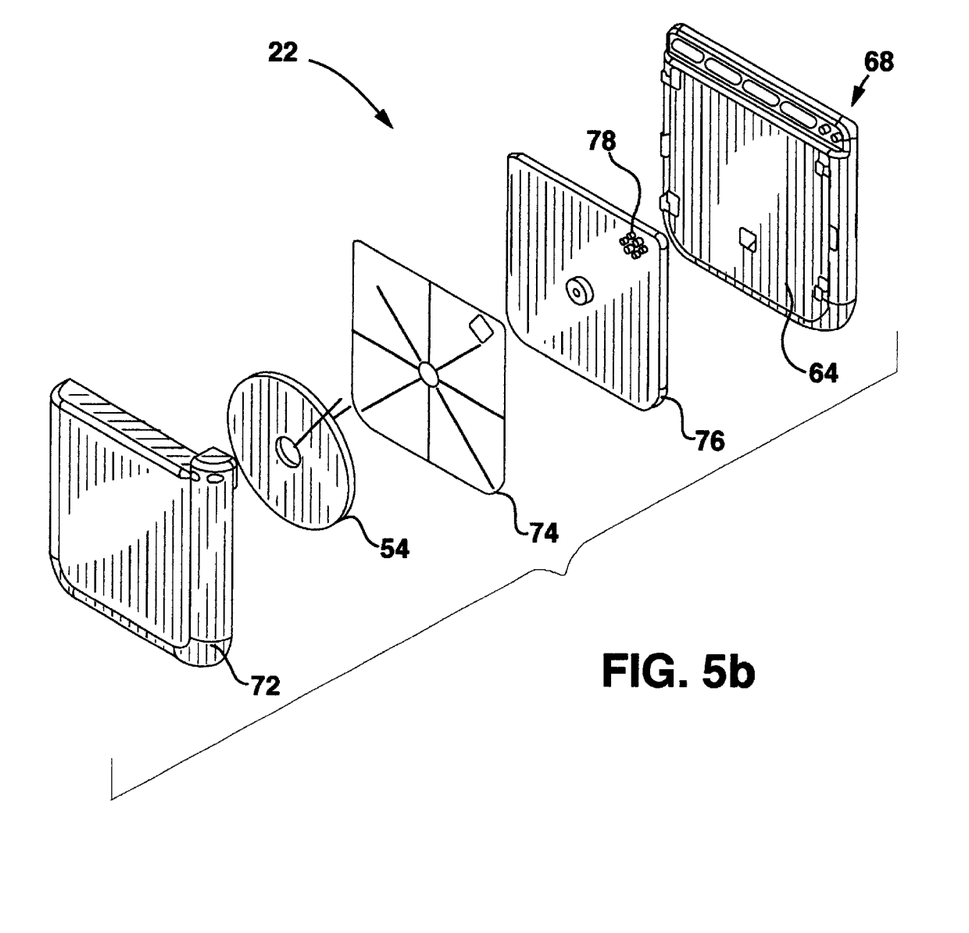

FIG. 5a shows an embodiment of a neuro stimulator 22 and FIG. 5b shows the neuro stimulator 22 with some external components in an exploded view. The external components include a coil cover 72, a recharging coil 54, a magnetic shield 74, and a coil carrier 76. The coil carrier 76 has at least one positioning detail 78 located between the recharging coil 54 and the recharging feedthrough 68 for positioning the electrical connection 56. The positioning detail 78 secures the electrical connection 56.

Figure 6A:
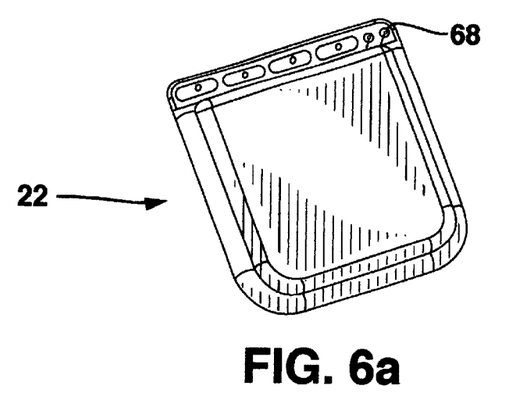
FIG. 6a shows another neuro stimulator embodiment.
Figure 6B:
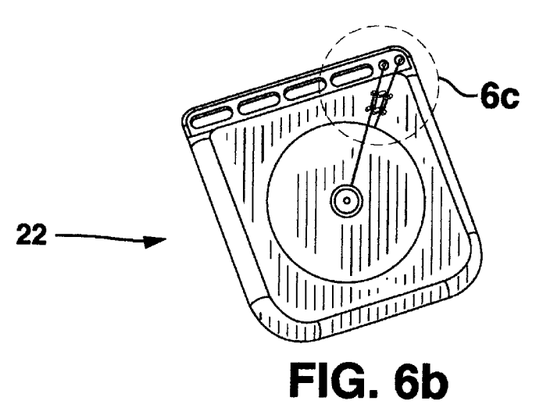
Figure 6C:
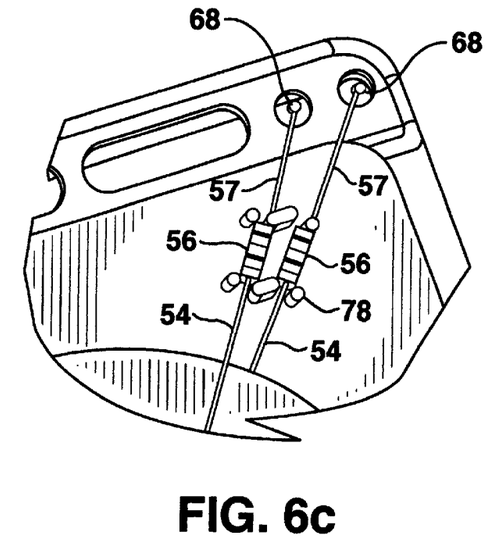
FIG. 6c shows an enlarged view of an electrical connection embodiment between the recharging coil and the recharge feedthrough shown in FIG. 6b.
Figure 7A:
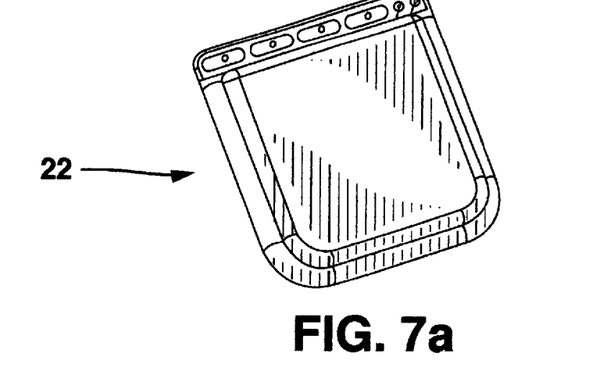
FIG. 7a shows another neuro stimulator embodiment.
Figure 7B:
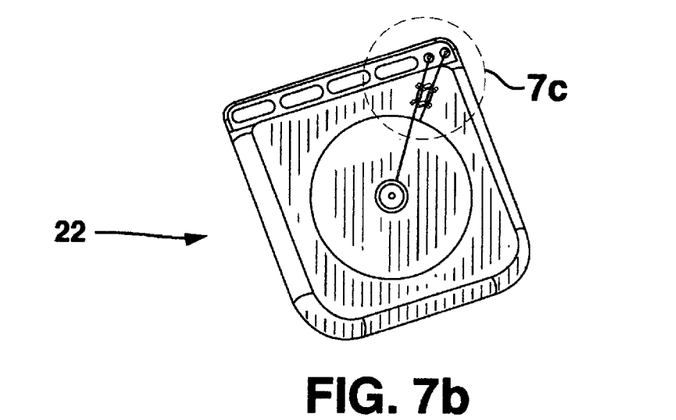
Figure 7C:
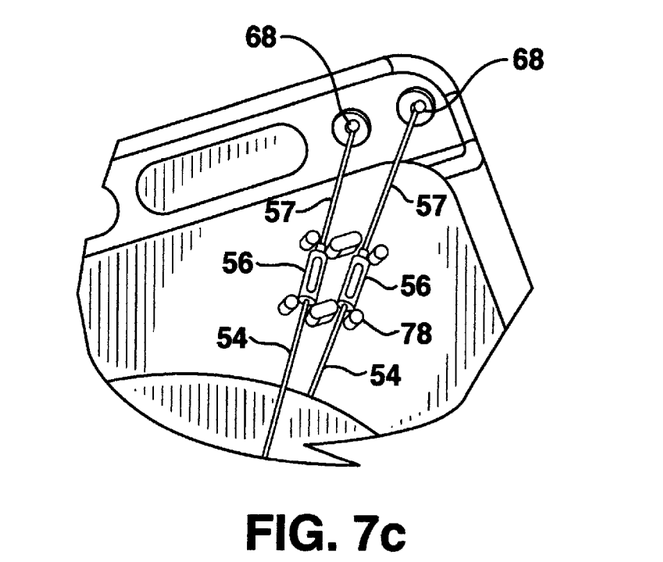
FIG. 7c shows an enlarged view of another electrical connection embodiment between the recharging coil and the recharge feedthrough shown in FIG. 7b.
Figure 8A:
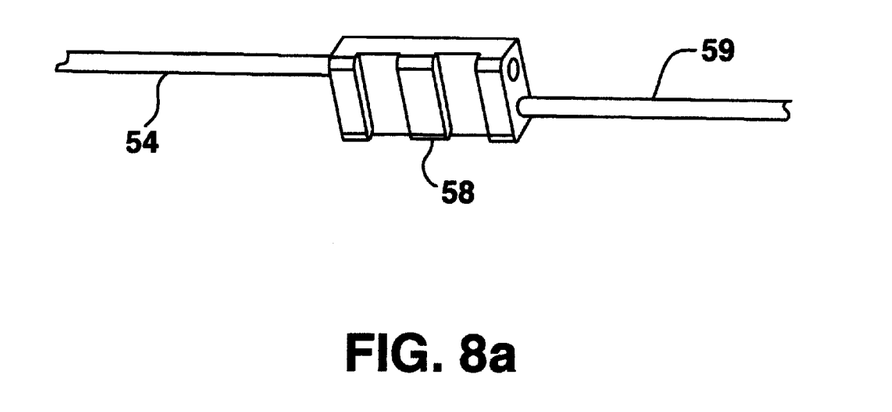
FIG. 8a shows a mechanical electrical connection embodiment.
Figure 8B:
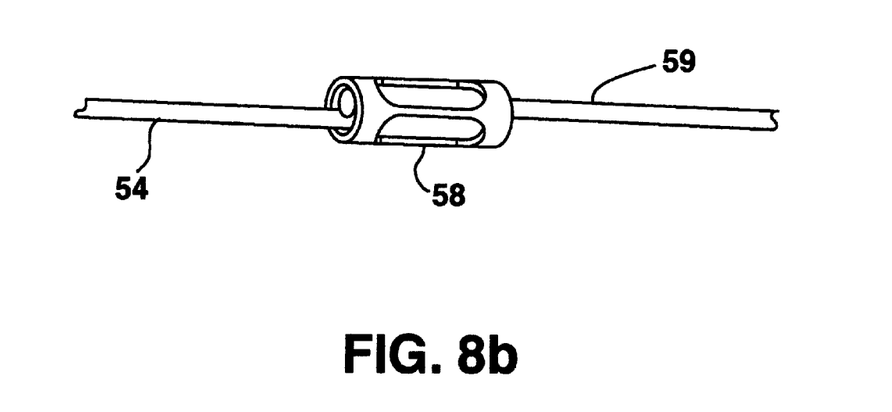
FIG. 8b shows another mechanical electrical connection embodiment.
Figure 8C:
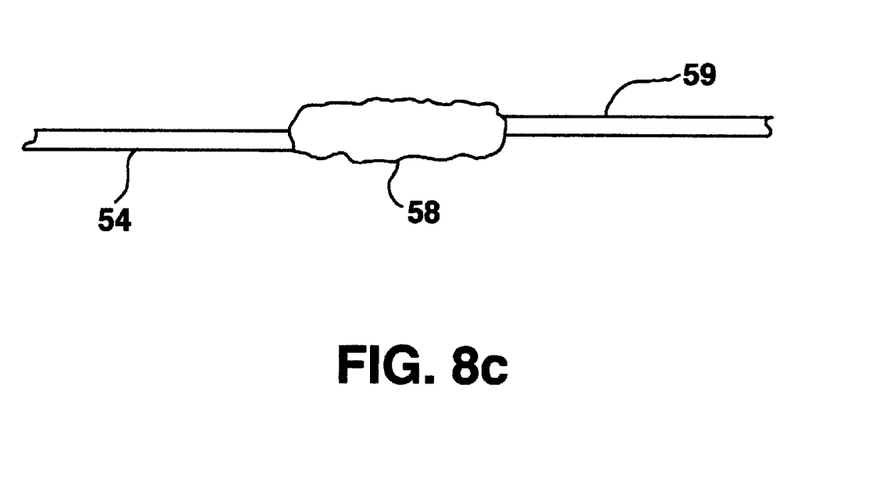
FIG. 8c shows a chemical electrical connection embodiment.

FIGS. 6a–6c show a neuro stimulator 22 embodiment with an electrical connection 56 embodiment. The recharge coil 54 is attached to an inert conductive metal with a crimp joint 58 embodiment that is secured in position with positioning details 78. FIGS. 7a–7c show the neuro stimulator 22 embodiment with another electrical connection 56 embodiment. The recharge coil 54 is attached to an inert conductive metal with another crimp joint 58 embodiment that is secured in position with positioning details 78. FIGS. 8a–8b show an enlarged view of the recharging coil 54 wire, crimp joint 58 embodiment, and connection wire 59. FIG. 8c shows an enlarged view of the recharging coil 54 wire, solder joint 58 embodiment, and connection wire 59.

Figure 9:
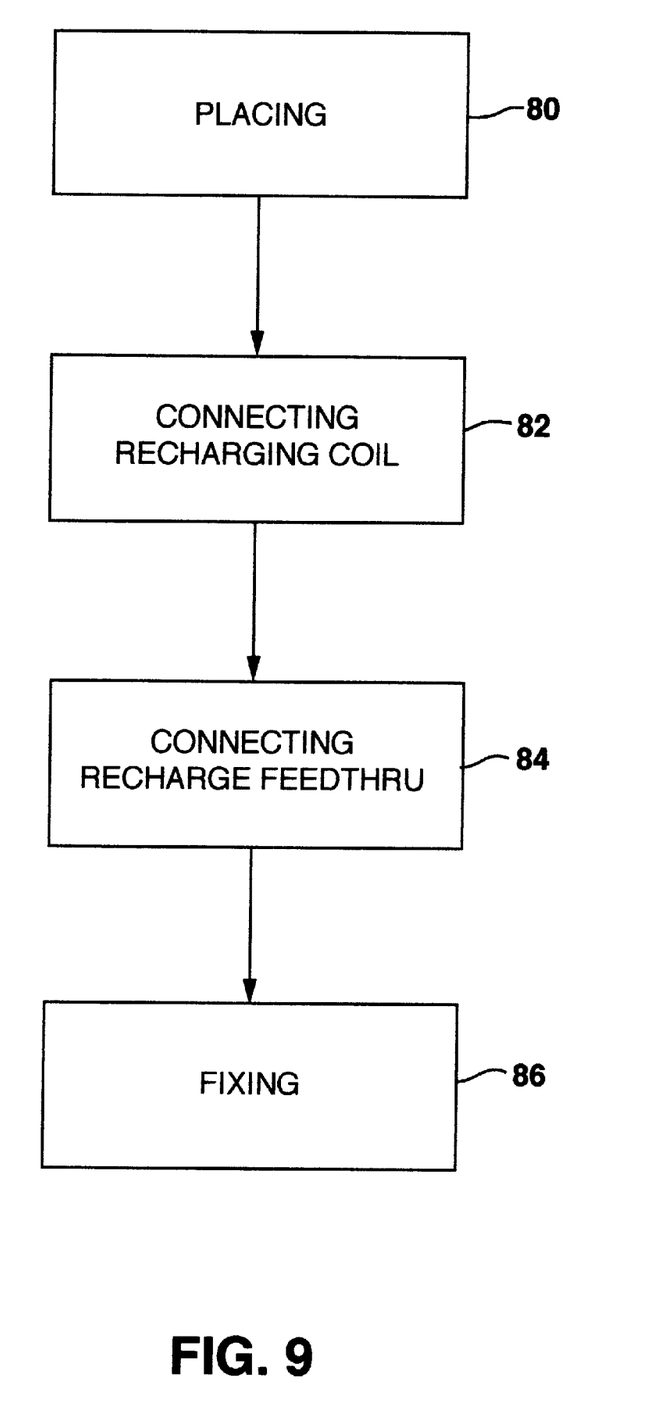
FIG. 9 shows a flowchart for forming an electrical connection embodiment.

FIG. 12 shows a flowchart for creating an electrical connection 56. The method for connecting a recharging coil 54 to a recharge feedthrough 68 in an implantable medical device 20 comprises the following elements. Placing 80 a recharging coil 54 on the housing exterior 64 of a medical device 20. Connecting the recharging coil 54 to an electrical connector. Connecting 82 the electrical connector 56 to a recharge feedthrough 68. Fixing 86 the electrical connector 56 in relation to the housing exterior 64. The method can also include protecting the electrical connection 56 with a hermetic seal 70.

Thus, embodiments of an implantable medical device 20 with an external recharging coil electrical connection are disclosed to provide an improved electrical connection between a external recharging coil 54 and a feedthrough 68. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device with recharging coil electrical connection, comprising:
   a housing having an interior cavity, an exterior surface, a therapy connection, and a recharge feedthrough;
   electronics carried in the housing interior cavity and configured to perform a medical therapy, the electronics being electrically connected to both the stimulation feedthrough and the recharge feedthrough;
   a rechargeable power source carried in the housing interior cavity and coupled to the electronics;
   a recharging coil carried on the housing exterior surface; and,
   at least one electrical connection manufactured from an inert conductive metal having a recharge coil connection and a recharge feedthrough connection, the electrical connection coupling the recharge coil to the feedthrough to couple the recharge coil to the electronics while reducing the opportunity for corrosion.

2. The implantable medical device as in claim 1 wherein the therapy connection includes a stimulation feedthrough.

3. The implantable medical device as in claim 2 wherein a recharge feedthrough is located away from the stimulation feedthrough to reduce interference.

4. The implantable medical device as in claim 1 wherein the therapy connection includes a drug infusion port.

5. The implantable medical device as in claim 1 wherein the therapy connection includes a physiological sensor input.

6. The implantable medical device as in claim 1 wherein the electrical connection is composed of an inert conductive metal resistant to corrosion.

7. The implantable medical device as in claim 6 wherein the inert conductive metal is selected from the group consisting of: niobum, titanium, and tantalum.

8. The implantable medical device as in claim 1 wherein the recharge coil connection is connected to the recharging coil with a mechanical connection.

9. The implantable medical device as in claim 8 wherein the mechanical connection is selected from the group consisting of: a crimp joint and a twist joint.

10. The implantable medical device as in claim 1 wherein the recharge coil connection is connected to the recharging coil with a chemical connection.

11. The implantable medical device as in claim 10 wherein the chemical connection is selected from the group consisting of: weld, braze joint, and solder joint.

12. The implantable medical device as in claim 1, further comprising a hermetic cover to protect the electrical connection.

13. The implantable medical device as in claim 12 wherein the hermetic cover is selected from the group comprising: potting material, epoxy, polysulforne, polyurethane, silicone rubber, polymer seal, and polymer encapsulation.

14. The implantable medical device with recharging coil feedthrough as in claim 1 wherein the recharge feedthrough is located on a housing proximal face.

15. The implantable medical device as in claim 1 wherein the medical device is selected from the group consisting of: neuro stimulators, drug delivery pumps, pacemakers, defibrillators, diagnostic recorders, and cochlear implants.

16. An implantable medical device with recharging coil electrical connection, comprising:
   a housing having an interior cavity, an exterior surface, a therapy connection, and a recharge feedthrough;
   electronics carried in the housing interior cavity and configured to perform a medical therapy, the electronics being electrically connected to both the stimulation feedthrough and the recharge feedthrough;
   a rechargeable power source carried in the housing interior cavity and coupled to the electronics;
   a recharging coil carried on the housing exterior surface;
   at least one electrical connection having a recharge coil connection and a recharge feedthrough connection, the electrical connection coupling the recharge coil to the feedthrough to couple the recharge coil to the electronics; and,
   at least one positioning detail located between the recharging coil and the recharging feedthrough for positioning the electrical connection wherein the positioning detail secures the electrical connection when a hermetic cover is applied.

17. An implantable medical device with recharging coil electrical connection, comprising:
   a housing having an interior cavity, an exterior surface, a therapy connection, and a recharge feedthrough;
   electronics carried in the housing interior cavity and configured to performed a medical therapy, the electronics being electrically connected to both the stimulation feedthrough and the recharge feedthrough;
   a rechargeable power source carried in the housing interior cavity and coupled to the electronics;
   a recharging coil carried on the housing exterior surface; and,
   a means for connecting, manufactured from an inert conductive material to couple the recharging coil to the recharge feedthrough to couple the recharging coil to the electronics while reducing the opportunity for corrosion.

18. The implantable medical device as in claim 17, further comprising a means for protecting to protect the means for connecting with a hermetic cover.

19. An exterior electrical connection for an implantable medical device, comprising:
   a recharging coil connection between a recharge coil and an electrical connector;
   a recharging feedthrough connection between a recharge feedthrough and the electrical connector; and,
   wherein the electrical connector is manufactured from a substantially inert metal resistant to corrosion.

20. The exterior electrical connector as in claim 19, further comprising a hermetic protective cover placed over exterior electrical connection.

21. A method of connecting an external recharging coil to a recharge feedthrough of an implantable medical device, comprising:

placing a recharging coil on the exterior of a housing of a medical device;

connecting the recharging coil to an electrical connector, the electrical connector being manufactured from an inert conductive material;

connecting the electrical connector to a recharge feedthrough, the recharge feedthrough being manufactured from a material other than copper;

fixing the electrical connector in relation to the housing; and, isolating the recharge coil from the recharge feedthrough by interposing an electrical connector manufactured from the inert conductive material to reduce the opportunity for corrosion.

22. The method in claim 21, further comprising: protecting the electrical connector with a hermetic seal.

* * * * *